United States Patent [19]

Dickinson

[11] Patent Number: 5,797,796
[45] Date of Patent: Aug. 25, 1998

[54] DATA ANALYSIS SYSTEM

[76] Inventor: Kenneth K. Dickinson, 3035 Green Valley Dr., Ann Arbor, Mich. 48103

[21] Appl. No.: 739,036

[22] Filed: Oct. 28, 1996

[51] Int. Cl.$^6$ .................................................... A63F 9/00
[52] U.S. Cl. ............................................................ 463/43
[58] Field of Search ................................ 463/43, 44, 45, 463/30, 31, 9, 4; 364/410, 411, 412

[56] References Cited

U.S. PATENT DOCUMENTS

| | | | |
|---|---|---|---|
| 4,918,603 | 4/1990 | Hughes et al. | 463/4 |
| 4,958,835 | 9/1990 | Tashiro et al. | |
| 4,968,257 | 11/1990 | Yalen | |
| 5,018,736 | 5/1991 | Pearson et al. | |
| 5,035,625 | 7/1991 | Munson et al. | 46/9 |
| 5,423,555 | 6/1995 | Kidrin | |
| 5,462,275 | 10/1995 | Lowe et al. | |
| 5,472,191 | 12/1995 | Hendricks | |

*Primary Examiner*—George Manuel
*Attorney, Agent, or Firm*—The Chupa Law Firm, P.C.

[57] ABSTRACT

A data system adapted to accept certain first data associated with a game situation and to forecast future plays in athletic contests. In one embodiment, the data system comprises: a data base containing said first data and further containing second data representing a plurality of probable future plays; a data analyzer adapted to recognize said certain first data and to retrieve said corresponding second data; and a user interface, adapted to accept said certain first data and to display said retrieved second data.

12 Claims, 5 Drawing Sheets

| PlayData Table | | | | | |
|---|---|---|---|---|---|
| Possession | Yardline | Territory | Play Number | Play Description | Play ID |
| A | 50 | A | 1 | Run, Right, RB, | |
| A | 50 | A | 2 | Run, Left, TB, | |
| A | 50 | A | 3 | Run, Left, FB, | |
| A | 50 | A | 4 | Pass, Middle, T | |
| A | 50 | A | 5 | Pass, Left, WR | |
| A | 0 | A | 6 | Run, Middle, QB | |

FIG. 4

DATA ANALYSIS SYSTEM

FIELD OF THE INVENTION

This invention relates to a computer based data analysis system and, more particularly, to computer based data analysis system which is adapted to receive data related to or defining a certain situation and/or condition and to use the received data to forecast the probability of future occurrences, such as and without limitation, types of plays in athletic contests.

DISCUSSION

Applicant has discovered that in competitive athletic contests, such as team events, participants and/or coaches often use a "favored" or "routine" play in certain game situations to coordinate teammates and to achieve a superior and/or desired result. Applicant has further discovered that a team or opponent may achieve a relatively large and decided advantage by predicting what play or type of play an opponent will "run" in a certain game situation. In this manner, the predicting opponent may strategically counter the opponent's plays, therefore vastly increasing the probability of "winning" the game.

Applicant has further discovered that one method of predicting what play or type of play an opponent will run is to study an opponent's past plays and the game situations in which those past plays were run. Since the number of plays and athletic team is capable of executing is finite, knowledge of what plays or type of plays and opponent has run under certain game situations is a reliable guide, as Applicant has found, for predicting what plays or type of plays an opponent will run under an identical or substantially similar game situations. Accordingly, Applicant has discovered the existence of a large or great need to reliably predict the type of plays that an opponent may use within an athletic contest. No such automated system currently exists to the best of Applicant's information and belief.

Applicant has discovered that the primary problem with the aforementioned prediction technique is that it involves an enormous amount of information. In order for an accurate prediction, numerous old game films must be studied and years of statistics must be compiled. Presently, coaches and players must often access their memories and/or countless documents to forecast a future play in an athletic contest. Due to the vast amount of information involved, an attempt to memorize or remember all potential game situations and all the plays which are run in those game situations is virtually impossible. This task is even more difficult considering that participants will often need to memorize new information for different opponents which they face on a weekly or daily basis. Moreover, because of the time constraints inherent in most athletic contests, coaches and players do not have the time to manually search a large "paper" type data base and make accurate predictions for game situations which are rapidly and continuously changing. Furthermore, an accurate "paper" type data base, which covers the multitude of different game situations which can arise in athletic contest, requires a large amount of paper and is relatively immobile, and thus burdensome in athletic contest where participants and coaches must be in constant movement and constantly focusing on the ever-changing game conditions.

There is therefore a need for a computer based and/or automated system which can be used to make accurate and relatively efficient forecasts of future plays in athletic contests. There is further a need for a data and/or computer based system that can store a large amount of data and make predictions relatively rapidly for a multitude of ever-changing game situations which may arise in an athletic contest. These and other needs are addressed by Applicant's invention. Moreover, it should be realized by those or ordinary skill in the art that the data base system of the preferred embodiment of the inventor may be adapted to receive data associated with non-athletic events and to predict the outcome of the future situations in a reliably predictable manner.

SUMMARY OF THE INVENTION

It is a first object of the invention to provide a computer based and/or automated data system which can be used to make accurate forecasts of future plays in athletic contests and which can store and retrieve past plays and associated game situations.

It is a second object of the invention to provide a computer based and/or automated data system which can rapidly make accurate forecasts of future plays in athletic contests for a multitude of different game situations.

It is a third object of the invention to provide a computer based and/or automated data system which can be used to make accurate forecasts of future plays in athletic contests and which may be adapted to use in a wide variety of other applications associated with non-athletic events.

According to one aspect of the present invention, a data system adapted to accept certain first data associated with a game situation and to forecast future plays in athletic contests is provided. According to the first aspect of the present invention, the system comprises a data base containing said first data and further containing second data representing a plurality of probable future plays which is associated with said first data; a data analyzer adapted to recognize said certain first data and to retrieve said corresponding second data; and a user interface, adapted to accept said certain first data and to display said retrieved second data, effective to allow one to accurately predict the occurrence of a certain future play.

According to a second aspect of the present invention, an automated data system adapted to accept certain first data associated with a game situation and to forecast future offensive plays and future defensive plays in athletic contest is provided. In one embodiment the system comprises a first data base containing data values representing past offensive plays and the corresponding situational game data representing the circumstances in which each said past offensive play was run; a second data base containing data values representing past defensive plays and the corresponding situational game data representing the circumstances in which each said past defensive play was run; a data analyzer effective and adapted to retrieve said past offensive and said past defensive plays which correspond to said present situational game data and calculate the approximate probability that each said past offensive and said past defensive play will be run; and a user interface, adapted to accept said present situational game data and to display data values representing the present situational game data, the past offensive and defensive plays and the probability that each of the past offensive plays and each of the past defensive plays will be run.

Further objects, features, and advantages of the present invention will become apparent from a consideration of the following description and the appended claims when taken in conjunction with the accompanying drawings.

BRIEF DESCRIPTION OF THE DRAWINGS

For a fuller and more complete understanding of the nature and objects of the present invention, reference should now be had to the following drawings in which:

FIG. 4 illustrates an offense database for use within and forming in one embodiment, an integral part of the preferred embodiment of the invention.

DETAILED DESCRIPTION OF THE INVENTION

Figure 1:
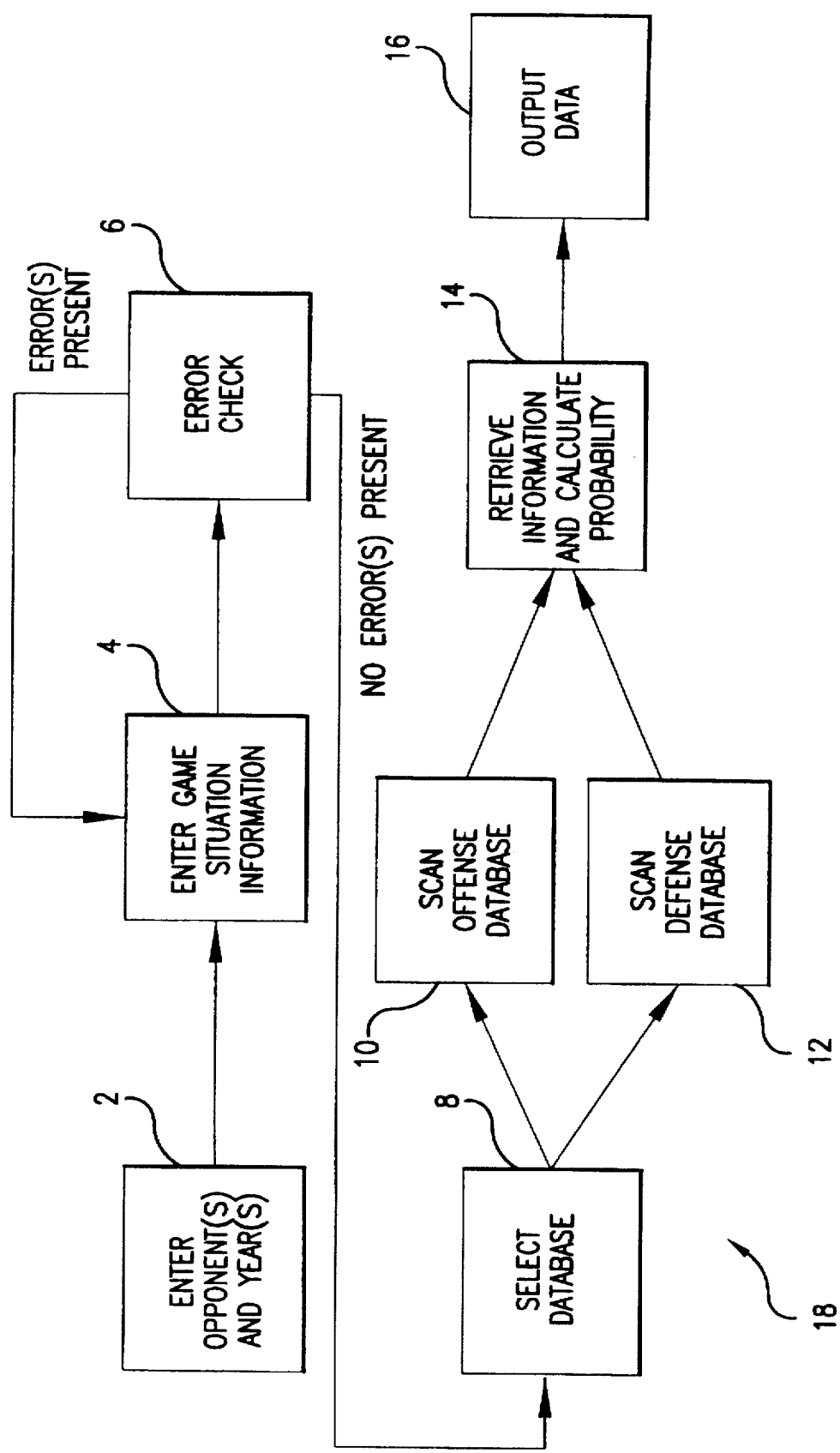
FIG. 1 is a block diagram of a methodology embodying the principles of the preferred embodiment of the invention and, in one embodiment of the invention, embedded within a software program.

Referring now to FIG. 1 there is shown a data analysis methodology 18 embodying the principles of the preferred embodiment of the present invention, and which is adapted for use within and automated computer based system to determine the probability of the occurrence of one of a plurality of athletic plays or occurrences. In the preferred embodiment of the invention, methodology 18 may be resident within and/or constructed by means of a computer program having a user interface program, such as and without limitation the conventional and commercially available Microsoft Visual Basic®, and a relational database program, such as and without limitation the conventional and commercially available Microsoft Access®. In the preferred embodiment of the invention the intended user is a player participant or a coach of a football or other type of athletic team. Moreover, the preferred embodiment of the invention is adapted to run on a microprocessor based or computer based automated type system running under stored program control.

Figure 2:
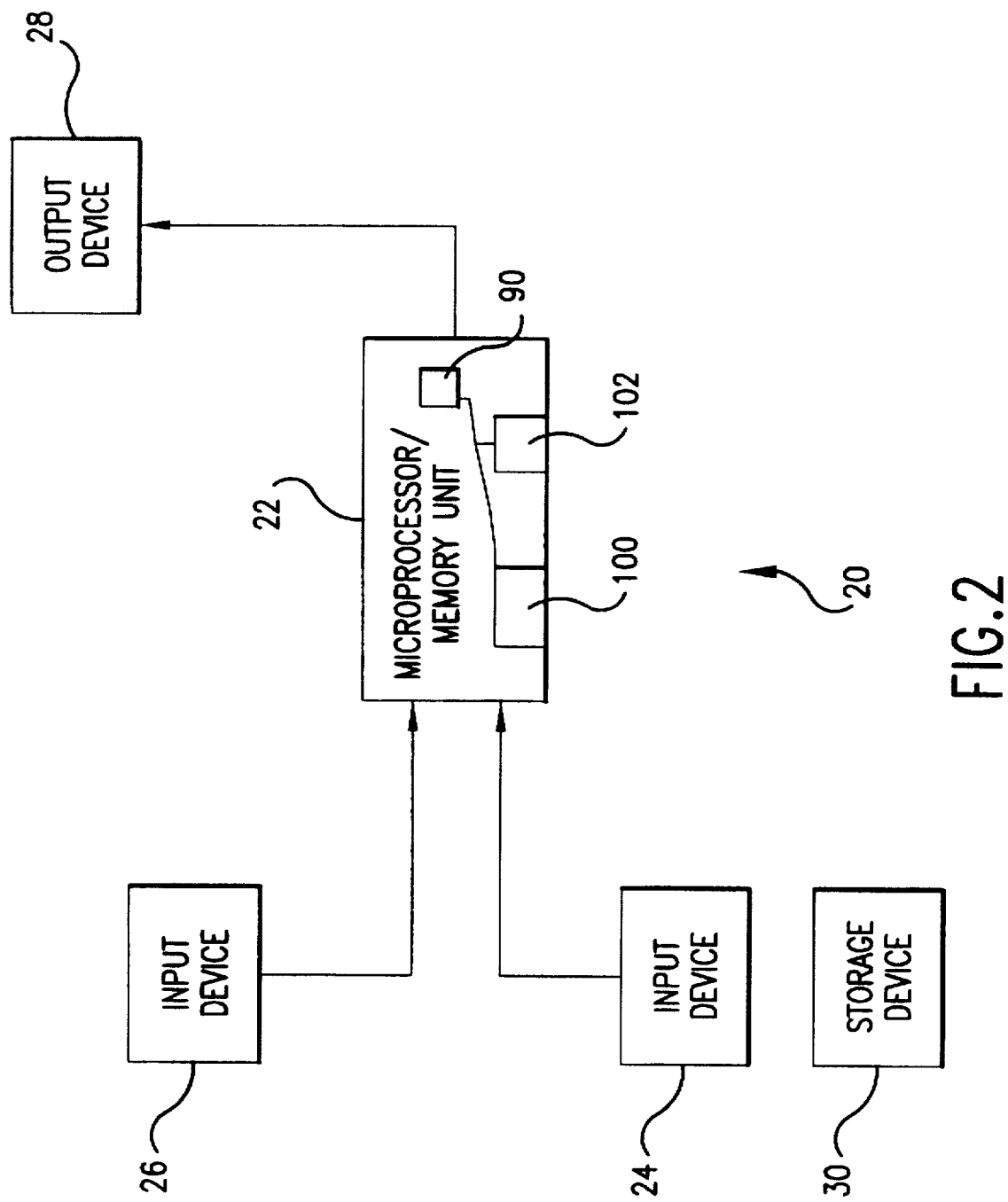
FIG. 2 is block diagram of a computer based system incorporating the principles of the preferred embodiment of the invention.

Referring now to FIG. 2 there is illustrated a microprocessor based system 20 suitable for use with the present invention. It should be apparent to one of ordinary skill in the art that other types of computer based systems, such as and without limitation the computer systems which are described and illustrated in Kai Hwang, "Advanced Computer Architecture", McGraw-Hill, Inc., 1993 (which is herein incorporated by reference, word for word and paragraph for paragraph) are similarly suitable and may be used with the principle of the present invention.

As shown, system 20 includes a microprocessor/memory unit 22 which is a suitable and commercially available computer having a conventional and commercially available microprocessor 90, such as and without limitation a Pentium 133®, which is electronically coupled to a random access memory (ram) 100 (temporary memory) and read only memory (rom) 102 (permanent memory). Input device 24, in one embodiment, comprises a suitable and commercially available device such as and without limitation a conventional and commercially available compact disk drive or a conventional or commercially available floppy disk drive, which is adapted to read data into the permanent and/or temporary memory of microprocessor/memory unit 22.

In the preferred embodiment of the invention, methodology 18 and the data used for the analysis is contained upon and/or within a conventional and commercially available storage device 30, which is in one embodiment, a conventional and commercially available compact disk or other storage device, and which is "loaded" into the memory of microprocessor/memory unit 22 through conventional and commercially available input device 24. Input device 26 in one embodiment, comprises a conventional and commercially available input device such as and without limitation a keyboard or a mouse, which is suitable to input data from a user of methodology 18. Output device 28 comprises, in one embodiment, a conventional and commercially available output device such as and without limitation a computer monitor or printer, which is suitable to display output generated by methodology 18 to a user.

Referring now to the methodology shown and described with respect to FIG. 1, as illustrated in block 2, a user of data system 20 initially selects preliminary information, such as and without limitation how many years of data the user desires to search and whether the user desires the information to pertain only to plays called when the current two teams play each other or to evaluate plays run by the opponent against and entire league or conference. This selection defines the scope of plays the relational database program will search, sort and retrieve. There is shown an example, in FIG. 3, of a user interface 40 for the preferred embodiment of the invention and a "pull-down" menu 42, which is selected by the user to enter the aforementioned preliminary information.

Referring now to FIG. 1, as illustrated by block 4, data system 20 (incorporating methodology 18) prompts the user for data describing the present game situation. The user enters the data into two sets of fields, "required" fields and "optional" fields. The "required" fields contain, in one embodiment, the minimum amount of information necessary for the relational database to conduct a search. The "optional" fields contain, in one embodiment, the information that can narrow the scope of a search but is not necessary for the relational database to conduct a search.

Figure 3:
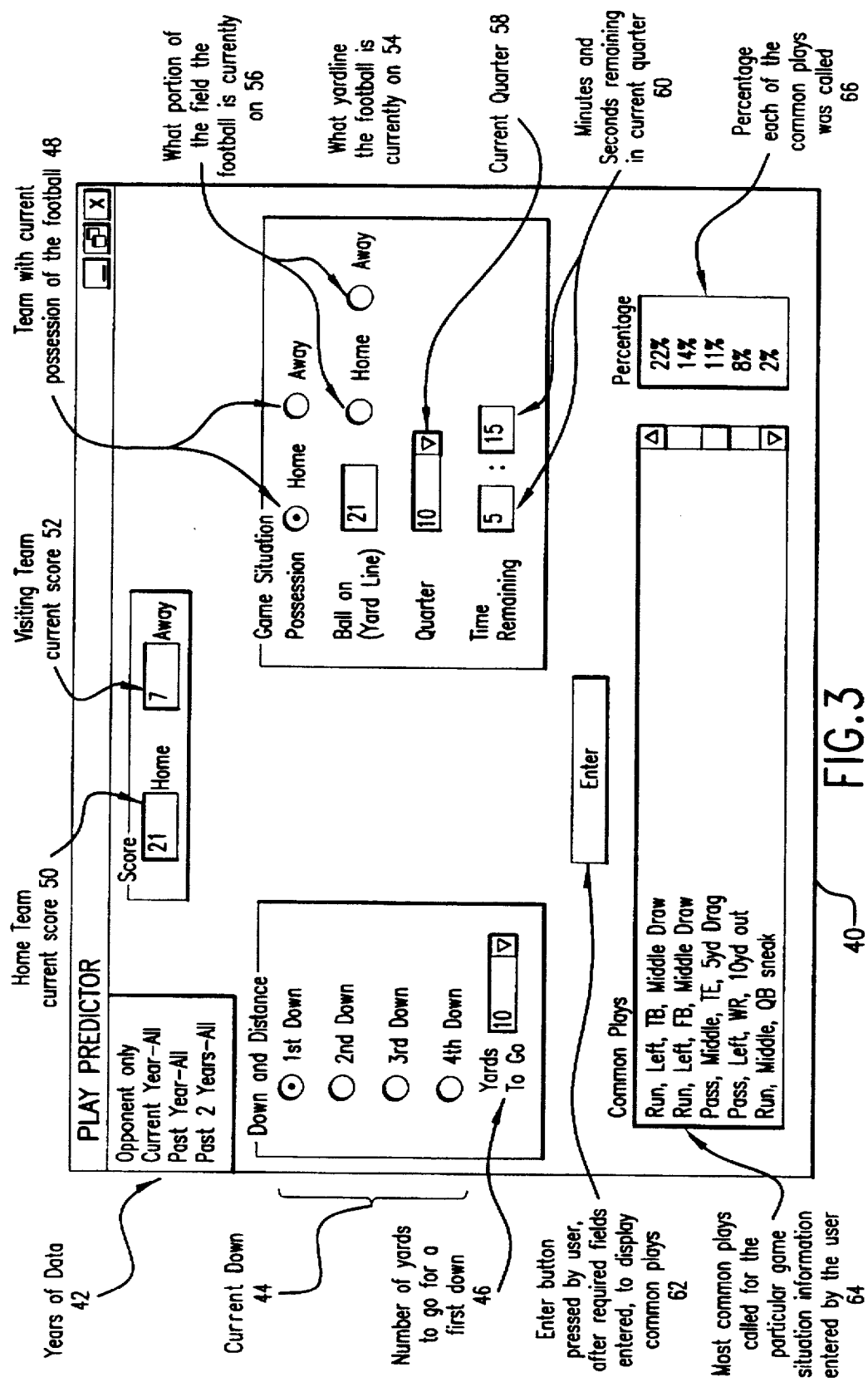
FIG. 3 illustrates one example of a user interface or display used by the computer based system made in accordance with the teachings of the preferred embodiment of the invention.

In the preferred embodiment of the invention, the required fields include:

"DOWN" which reflects the current down in the game being analyzed and which has valid values of 1, 2, 3 and 4. "DOWN" is illustrated by field 44 in user interface 40, FIG. 3;

"DISTANCE" which reflects, through a range value, the number of yards needed to achieve a first down for the game situation being analyzed (the relational database program translates the number entered into one of the following pre-defined range codes: D1_3 (a distance of one (1) to three (3) yards), D4_6 (a distance of four (4) to six (6) yards), D7_10 (a distance of seven (7) to ten (10) yards), and D10 (a distance greater than ten (10) yards)). "DISTANCE" is illustrated by field 46 in user interface 40, FIG. 3;

"POSSESSION" which reflects whether the team whose data is being analyzed (i.e. the opponent's team), is "on offense" (i.e. has possession of the football) or is "on defense" and which has valid values of "O" (offense) and "D" (defense). "POSSESSION" is illustrated by field 48 in user interface 40, FIG. 3; In the preferred embodiment of the invention, the optional fields include:

"NET_SCORE" which reflects a range of game scores based on the value obtained by subtracting the "Away" team's score (the value of which is entered by the user, and is illustrated by field 52 in user interface 40, FIG. 3) from the "Home" team's score (the value of which is entered by the user, and is illustrated by field 50 in user interface 40, FIG.

3). Data system 18 calculates the difference and determines the appropriate value for "NET_SCORE", which has valid values of: "TIED" (Tie score, difference is zero), "HTW1_3" (Home team is winning by one (1) to three (3) points), "HTW4_7" (Home team is winning by four (4) to seven (7) points), "HTW8_10" (Home team is winning by eight (8) to ten (10) points), "HTW11_14" (Home team is winning by eleven (11) to fourteen (14) points, "HTW15" (Home team is winning by more than fifteen (15) points, "HTL1_3"" (Home team is losing by one (1) to three (3) points), "HTL4_7" (Home team is losing by four (4) to seven (7) points), "HTL8_10" (Home team is losing by eight (8) to ten (10) points), "HTL11_14" (Home team is losing by eleven (11) to fourteen (14) points, and "HTL15" (Home team is losing by more than fifteen (15) points);

"YARDLINE" which reflects, through a range value, the numeric yard marker on the field where the football is located. Since a football field is divided into two fifty (50) yard segments, the user must enter the "yardline" (illustrated by field 54 in user interface 40, FIG. 3) and the "territory" (home team's or away team's, illustrated by field 56 in user interface 40, FIG. 3) for data system 18 to determine the appropriate value for "YARDLINE", which has valid values of: "HL_5" (Home team's territory inside the five (5) yardline), "H6_10" (Home team's territory between the six (6) and ten (10) yardline), "H11_20" (Home team's territory between the eleven (11) and twenty (20) yardline), "H21_30" (Home team's territory between the twenty-one (21) and thirty (30) yardline), "H31_40" (Home team's territory between the thirty-one (31) and forty (40) yardline), "H41_50" (Home team's territory between the forty-one (41) and fifty (50) yardline), "AL-5" (Away team's territory inside the five (5) yardline), "A6_10" (Away team's territory between the six (6) and ten (10) yardline), "A11_20" (Away team's territory between the eleven (11) and twenty (20) yardline), "A21_30" (Away team's territory between the twenty-one (21) and thirty (30) yardline), "A31_40" (Away team's territory between the thirty-one (31) and forty (40) yardline), and "A41_50" (Away team's territory between the forty-one (41) and fifty (50) yardline);

"QUARTER" which reflects the current quarter for the game situation being analyzed and has valid values of one (1) (first quarter), two (2) (second quarter), three (3) (third quarter), four (4) (fourth quarter) and five (5) (overtime). "QUARTER" is illustrated by field 58 in user interface 40, FIG. 3;

"MINUTES_REM" which reflects, through a range value, the minutes remaining in the current quarter, for the game situation being analyzed (the relational database program translates the number entered into one of the following pre-defined range codes: MO_SL30 (zero minutes and less than thirty (30) seconds remaining), MO_SG30 (zero minutes and greater than thirty (30) seconds)), M1_2 (one (1) to two (2) minutes remaining), M3_5 (three (3) to five (5) minutes remaining), M6_10 (six (6) to ten (10) minutes remaining), and M11_15 (eleven (11) to fifteen (15) minutes remaining). "MINUTES_REM" is illustrated in field 60 of user interface 40, FIG. 3; and "SECONDS_REM" which reflects the seconds remaining, through a range value, in the current minutes remaining ("MIN_REM") in the current quarter for the game situation being analyzed. "SECONDS_REM" is determined by data system 18 by translating the user-entered seconds into one of the following range codes: SL30 (less than thirty seconds) and SG30 (greater than thirty seconds). The relational database program only uses the SECONDS_REM value when the MINUTES_REM value is equal to zero. "SECONDS_REM" is illustrated in field 60 of user interface 40, FIG. 3.

The game situation data is "translated" by the relational database into the database formats described above and is saved in a database table. In the preferred embodiment of the invention, Microsoft Access® "translates" the game situation data into the appropriate fields by use of the "sorting" function; a database table is created with the ® "CREATE TABLE" function; and the data is saved in the database table by use of "SAVE TABLE" function.

After the user enters the game situation data, the user, in the preferred embodiment of the invention, is required to select an enter function (illustrated by field 62, FIG. 3). Data system 20 then performs an error validation, illustrated by block 6, FIG. 1 to ensure that all required fields contain information and that all fields are in the correct format (e.g. numerical fields contain numbers) and represent possible game situations. For example, in the preferred embodiment of the invention, the error validation checks to ensure that all numerical fields contain numbers, the "DISTANCE" field is less than one hundred (100), the "YARDLINE" field is less than or equal to fifty (50), the "MINUTES_REM" field is less than or equal to fifteen (15); and the "SECONDS_REM" field is less than or equal to fifty-nine (59). If an error is present, data system 20 issues a message indicating the type of error and permits the user to re-enter the necessary game situation data.

Once the user enters all data in the required fields and in the correct format, data system 18 selects one of two databases, offense or defense, to be searched based on the entry in the "POSSESSION" field, as illustrated in block 8. If the opponent being analyzed is "on defense", data system 20 will search the defense database containing past defensive plays, illustrated by block 12. If the opponent being analyzed is "on offense", data system 18 will search the offense database containing past offensive plays, illustrated by block 10. A portion of a sample offense database 70 is illustrated in FIG. 4.

Each play contained in the offense and defense databases has an identification code and a description which define the play.

The textual description for each play is contained in the database elements "O_PLAY_DESC" (offense play descriptions) and "D_PLAY_DESC" (defense play descriptions). The contents of "O_PLAY_DESC" and "D_PLAY_DESC" are determined from analyzing and recording all actual football game plays. The components of the "O_PLAY_DESC" database include: run/pass; the general location of the run (right, middle, left); detailed location of the run (e.g. center, guard, tackle, sweep, etc.) or pass (screen, five (5) yard cross, ten (10) yard cross, curl, fly, out, post, etc.); and player position who ran/threw/caught football (quarterback, running back, full back, tight end, wide receiver, etc.). The components of the "D_PLAY_DESC" database include: defensive alignment (5–2, 4–3, etc.); defensive secondary coverage (two-deep, three-deep); and scheme (e.g. linebacker blitz, defensive lineman stunt, etc.).

The identification code for each play is contained in the database element "PLAY_ID". The "PLAY_ID" is a three (3) character code that corresponds with a play description ("O_PLAY_DESC" or "D_PLAY_DESC") and allows for easier processing and sorting of play information.

Also contained in the offense and defense databases is the associated data describing the game situation in which each past play was run. As illustrated by block 14, data system 20 retrieves all plays that have associated game situation data which is substantially similar to the game situation data that was entered by the user (i.e. data system 20 retrieves all past plays an opponent has run when faced with a situation similar to the present user's).

In the preferred embodiment of the invention, the "retrieval" step illustrated by block 18 is performed by Microsoft Access®. Data system 20 translates the game situation data entered by the user into database format, as previously described, and a database "SELECT" command is used to retrieve all rows where the screen values (now translated into system variables) are equal to the same field values stored in the offense or defense database, depending on the value in the "POSSESSION" field.

Data system 20 also calculates the percentage that each play has been run, representing an approximate probability that each play will be run in the present game situation. In the preferred embodiment of the invention, the "calculate" step is performed by Microsoft Access®. The percentage displayed is determined by the "CALCULATE" function and is defined by following equation: Percentage=(Number of plays retrieved having the same identification code)/ (Number of total plays retrieved)×100%. Other probability/ percentage calculations may be used including those set forth in the text entitled *Engineering Statistics* which was published by Prentice-Hall in 1972, authored by Bowker and Lieberman, has a catalogue number ISBN-0-13-279455-1, and which is fully and completely incorporated herein by reference, word for word and paragraph for paragraph.

As illustrated by block 16, data system 18 outputs all the retrieved play information and displays the play description and the percentage that each play was run for the given game situation. In the preferred embodiment of the invention, the Microsoft Visual Basic® "DISPLAY" command is used to display the play description and its associated percentage. The play description is illustrated by field 64 in user interface 40, FIG. 3 and the percentage is illustrated by field 66 in user interface 40, FIG. 3.

Further information may be contained in the offensive and defensive database and can be retrieved and displayed to the user in a substantially similar manner. Other information includes without limitation: the opposing team which the plays were run against, the date of the game when the data was gathered, the "play number" representing the sequential number of a given play in a given game, the opposing coach of the team, whose data is being analyzed, when the data was gathered, and whether the team whose data is being analyzed was the home or away team during the game where the play information was gathered. It should be apparent to one of ordinary skill in the art that both the offense and defense databases may be contained and/or physically stored as two distinct database tables located within a single relational database (likely stored on one commercially available CD-ROM disk). Alternatively, the two databases may be stored on separate disks and/or reside within separate databases.

While nearly any user interface program can be used in conjunction with nearly any relational database program to achieve the desired result, the inventor has successfully designed, tested and used the present invention using Microsoft Visual Basic® as the user interface program and Microsoft Access® as the relational database program. However, as will be known to those of ordinary skill in the art, other commercially available databases may be used such as, and without limitation, the Oracle® database.

Figure 5:
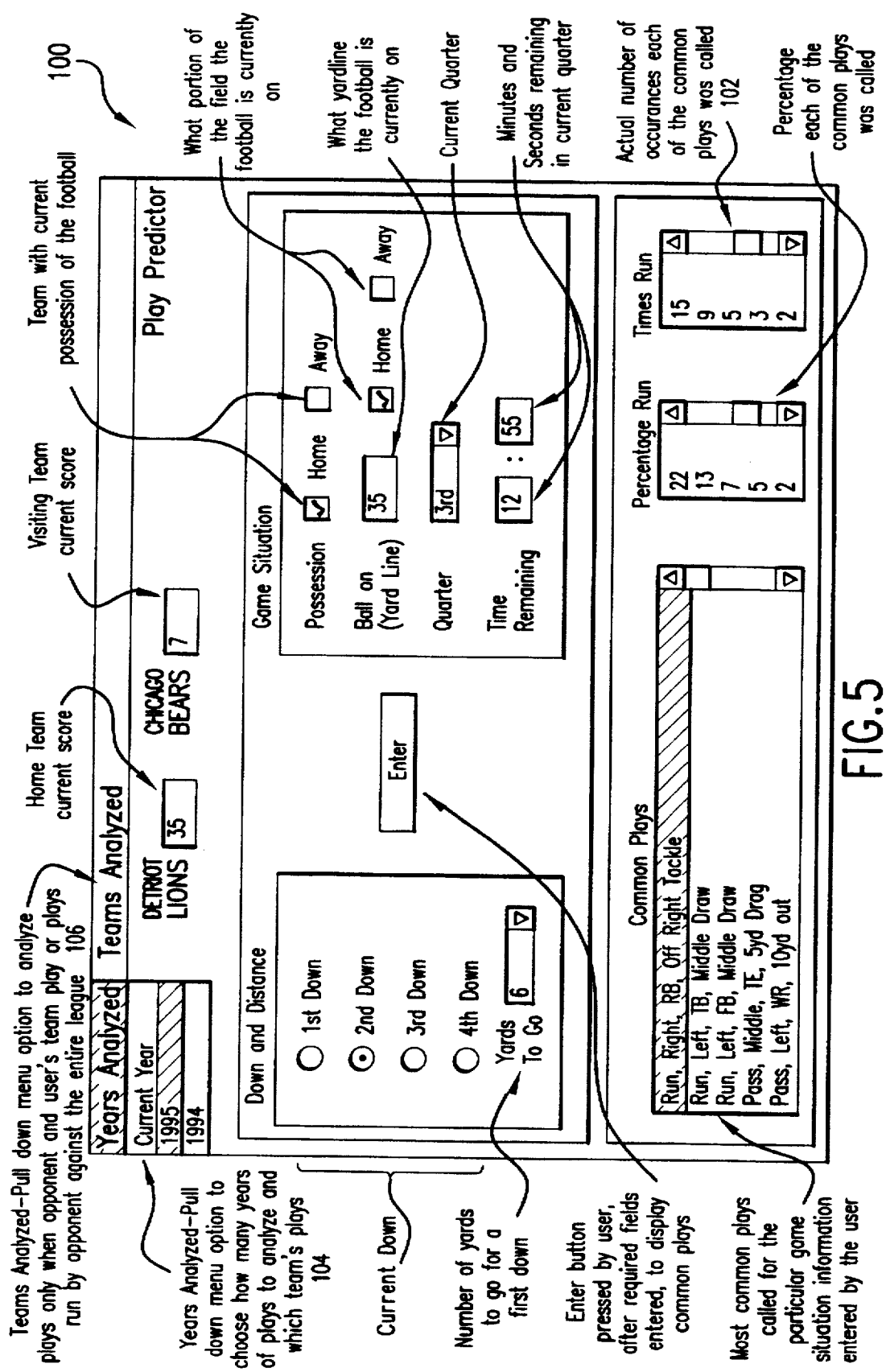
FIG. 5 illustrates a second example of a user interface or display used by the computer based system made in accordance with the teachings of the preferred embodiment of the invention.

Referring now to FIG. 5 there is shown a user interface and/or interactive screen 100 which differs from the user interface and/or interactive screen 40 by the addition of the "times run" data field 102 which provides the user with the actual number of occurrences each of the common plays were called. This data, in one embodiment, resides within offensive and defensive database 10, 12, as shown in FIG. 1. Moreover, screen 100 also includes a "years analyzed" data field 104 which, in one embodiment, comprises a "pull down" menu which allows a user to choose the number of years of data which shall be analyzed by system 18. In this embodiment, the data found in databases 10 and 12 are tagged with a year that the plays first occurred and which are represented by the stored data. With this "year tag", field 104 may be used as a "soft filter" to allow a user to select only a portion of the stored data.

Finally data interface/interactive screen 100 includes a "teams analyzed" data field 106 which, in one embodiment, comprises a pull down menu which allows a user to select only data, from databases 10 and 12, associated with the plays occurring when the two presently playing teams are engaged, or to select plays which are run throughout the entire league.

It should be understood, however, that the invention is not limited to the exact construction, programs or method illustrated and described above, but that various changes and modifications may be made without departing from the spirit and scope of the invention as defined in the following claims. Moreover, it should be further understood that the afore-described invention may be modified for use in non-athletic contests such as, and without limitation in jury selection situations. The principles of the preferred inventions involve analyzing past situations to determine the characteristics of the past situations, the chosen occurrences, and the result emanating from the chosen occurrences. This compiled data base may then be used to reasonably accurately predict the future occurrence of future events.

I claim:

1. A data system adapted to accept certain first data associated with a game situation and to forecast future plays in athletic contests, said system comprising:
   a data base containing said first data and further containing second data representing a plurality of probable future plays;
   a data analyzer adapted to recognize said certain first data and to retrieve said corresponding second data; and
   a user interface, adapted to accept said certain first data and to display said retrieved second data.

2. The data system of claim 1 wherein said second data represents a plurality of probable future defensive plays.

3. The data system of claim 1 wherein said second data represents a plurality of probable future offensive plays.

4. The data system of claim 1 wherein said data analyzer is further adapted to calculate the approximate probability that each said future play will occur.

5. The data system of claim 1 wherein said athletic contests are football games.

6. The data system of claim 1 wherein said user interface is a Microsoft Visual Basic® program.

7. The data system of claim 1 wherein said data base and said data analyzer are Microsoft Access® implementations.

8. A data system adapted to accept certain first data associated with a game situation and to forecast future offensive plays and future defensive plays in athletic contests, said system comprising:
   a first data base containing data values representing past offensive plays and the corresponding situational game data representing the circumstances in which each said past offensive play was run;

a second data base containing data values representing past defensive plays and the corresponding situational game data representing the circumstances in which each said past defensive play was run;

a data analyzer effective to retrieve said past offensive and said past defensive plays which correspond to said present situational game data and calculate the percentage that each said past offensive and said past defensive play was run; and a user interface, adapted to accept said present situational game data and display data values representing said present situational game data, said past offensive and defensive plays and said percentage that each said past offensive play and each said defensive play was run.

9. The data system of claim 8 wherein said athletic contests are football games.

10. The data system of claim 8 wherein said user interface is a Microsoft Visual Basic® program.

11. The data system of claim 8 wherein said first data base, said second data base and said data analyzer are Microsoft Access® implementations.

12. A method of predicting future games in athletic contests, which comprises the steps of:

storing certain first data describing past plays and certain second data associated with said first data and describing the game situations, in which said past plays were run, in a first database;

accepting certain third data describing a present game situation;

searching said first database for any of said second data which is substantially similar to said third data;

retrieving any of said second data which is substantially similar to said third data and any of said first data associated with said second data which is substantially similar to said third data;

displaying any of said first data associated with said second data which is substantially similar to said third data.

* * * * *